(12) United States Patent
Isaacson et al.

(10) Patent No.: US 9,480,408 B2
(45) Date of Patent: Nov. 1, 2016

(54) HOME UTERINE ACTIVITY MONITORING

(75) Inventors: Philip O. Isaacson, Chanhassen, MN (US); Bryant Austin Jones, Minnetonka, MN (US); Timothy L. Johnson, Plymouth, MN (US)

(73) Assignee: Nonin Medical, Inc., Plymouth, MN (US)

(*) Notice: Subject to any disclaimer, the term of this patent is extended or adjusted under 35 U.S.C. 154(b) by 0 days.

(21) Appl. No.: 13/484,888

(22) Filed: May 31, 2012

(65) Prior Publication Data
US 2012/0304784 A1 Dec. 6, 2012

Related U.S. Application Data

(60) Provisional application No. 61/492,648, filed on Jun. 2, 2011.

(51) Int. Cl.
| | |
|---|---|
| *G01L 1/00* | (2006.01) |
| *G01L 5/00* | (2006.01) |
| *A61B 5/03* | (2006.01) |
| *A61B 5/00* | (2006.01) |

(52) U.S. Cl.
CPC ............ *A61B 5/033* (2013.01); *A61B 5/6831* (2013.01); *A61B 5/6843* (2013.01)

(58) Field of Classification Search
CPC ............ G01L 5/04; A61B 5/033; G06F 3/03
USPC ........................................ 73/862.381, 862.42
See application file for complete search history.

(56) References Cited

U.S. PATENT DOCUMENTS

| 4,949,730 A | 8/1990 | Cobben et al. |
| 4,966,152 A * | 10/1990 | Gang et al. .................. 600/453 |
| 4,987,898 A | 1/1991 | Sones |
| 5,645,563 A | 7/1997 | Hahn et al. |
| 5,800,337 A | 9/1998 | Gavish |
| 6,048,323 A * | 4/2000 | Hon ............................ 600/588 |

(Continued)

FOREIGN PATENT DOCUMENTS

| JP | 49103796 U | 9/1974 |
| JP | 49151079 U | 12/1974 |

(Continued)

OTHER PUBLICATIONS

"International Application Serial No. PCT/US/2012/040135, International Report on Patentability mailed Dec. 2, 2013", 6 pgs.

(Continued)

*Primary Examiner* — Lisa Caputo
*Assistant Examiner* — Roger Hernandez-Prewit
(74) *Attorney, Agent, or Firm* — Schwegman Lundberg & Woessner, P.A.

(57) ABSTRACT

A device includes a guard member, at least one bias sensor, a display, and a measurement sensor. The guard member includes an aperture on an axis. The at least one bias sensor is coupled to the guard member. The at least one bias sensor is configured to provide a bias signal corresponding to a bias force on the guard member. The bias force is aligned parallel with the axis. The display is coupled to the at least one bias sensor and is configured to provide a visible indication of the bias force. The measurement sensor is configured to provide an output signal corresponding to a measured force proximate the aperture.

19 Claims, 4 Drawing Sheets

(56) References Cited

U.S. PATENT DOCUMENTS

| | | | |
|---|---|---|---|
| 6,831,629 B2* | 12/2004 | Nishino et al. | 345/157 |
| 2002/0133310 A1* | 9/2002 | Tamura | 702/139 |
| 2005/0264530 A1* | 12/2005 | Takatsuka | G06F 3/0338 |
| | | | 345/160 |
| 2006/0149168 A1 | 7/2006 | Czarnek | |
| 2007/0032726 A1 | 2/2007 | Osaka et al. | |
| 2007/0213616 A1* | 9/2007 | Anderson et al. | 600/448 |
| 2009/0163795 A1 | 6/2009 | Czarnek | |
| 2009/0234206 A1 | 9/2009 | Gaspard et al. | |
| 2010/0240967 A1 | 9/2010 | Kim et al. | |

FOREIGN PATENT DOCUMENTS

| | | |
|---|---|---|
| JP | 63501196 A | 5/1988 |
| JP | 10302188 A | 11/1998 |
| JP | 2000503863 A | 4/2000 |
| JP | 2003325464 A | 11/2003 |
| JP | 5734201 B2 | 6/2015 |
| WO | WO-2012166866 A1 | 12/2012 |

OTHER PUBLICATIONS

"International Application Serial No. PCT/US/2012/040135, Search Report mailed Aug. 31, 2012", 4 pgs.

"International Application Serial No. PCT/US/2012/040135, Written Opinion mailed Aug. 31, 2012", 5 pgs.

Smyth, C. N., et al., "The Guard-Ring Tocodynamometer: Absolute Measurement of Intra-Amniotic Pressure by a New Instrument", BJOG: An International Journal of Obstetrics & Gynaecology, 64(1), (Feb. 1957), 59-67.

European Application Serial No. 1272494.2, Office Action mailed Jan. 22, 2014, 2 pgs.

European Application Serial No. 12724942, Response filed Jul. 31, 2014 to Office Action mailed Jan. 22, 2014, 15 pgs.

Japanese Application Serial No. 2014-513679, Office Action mailed Mar. 8, 2016, (w/ English Translation), 7 pgs.

* cited by examiner

HOME UTERINE ACTIVITY MONITORING

CLAIM OF PRIORITY

This patent application claims the benefit of priority, under 35 U.S.C. Section 119(e), to Philip O. Isaacson, U.S. Provisional Patent Application Ser. No. 61/492,648, entitled "HOME UTERINE ACTIVITY MONITORING," filed on Jun. 2, 2011, which is hereby incorporated by reference herein in its entirety.

BACKGROUND

Intra-uterine pressure can be used to monitor health of a pregnant woman. Technology for measuring such a pressure (sometimes referred to as intra-amniotic pressure) is described in the 1957 article by C. N. Smyth entitled "The Guard-Ring Tocodynamometer." Current technology for noninvasively measuring pressure is inadequate.

OVERVIEW

A guard ring is positioned on the abdomen. The guard ring includes an aperture. One or more force sensors on the guard ring provides an electric signal corresponding to the pressure exerted by the guard ring on the tissue of the abdomen. A visual display indicates the pressure exerted by the guard ring. The guard ring biasing pressure can be adjusted by a belt coupled to the guard ring and configured to encircle a portion of the body.

The display can indicate a suitable pressure on the guard ring for reliable measurement of an intra-uterine pressure. The intra-uterine pressure is measured by a force sensor positioned to read a pressure on the tissue at the aperture. One or both of the guard ring pressure and the intra-uterine pressure are telemetered to a remote device. In one example, one or both of the pressures are indicated on the visual display.

One example can be configured to measure intra-uterine pressure of a pregnant woman. Other applications are also included. For example, an absolute pressure of an eye can be measured by a suitably configured example. Other bodily pressures can also be monitored or measured by other examples of the present subject matter.

The present inventors have recognized, among other things, that a problem to be solved can include monitoring or measuring intra-uterine pressure. The present subject matter can help provide a solution to this problem, such as by using a guard ring and a suitably configured pressure sensor. In one example, a first pressure sensor aids in establishing a suitable biasing force on the guard ring and a second pressure sensor provide a measure of force exerted on tissue at an aperture of the guard ring.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A guard ring can be positioned atop tissue to exert a biasing force in a direction normal to the abdomen. The guard ring can be fabricated of a rigid material having an aperture in a center portion. A force on the guard ring creates a flattened area of tissue and the tissue adjacent the aperture forms an elastic membrane. The membrane can include tissue at the abdomen as well as clothing, dressing, or bedding materials. A force measurement of the tissue adjacent the aperture can provide an indication of the absolute pressure of, for example, amniotic pressure.

A suitable force on the guard ring assures that the force measured at the aperture accurately reflects the internal pressure. A force insufficient to form a suitably flattened region of tissue or a force too great will both lead to inaccurate pressure measurement at the aperture. In various examples, the force should be in the range of 1 to 2 kg over an approximately 3-inch diameter guard ring. This is approximately 20 to 40 grams per square centimeter.

The force on the guard ring can be measured by various configurations of one or more sensors. For example, a pair of sensors equally spaced about the guard ring periphery can provide an indication of the biasing force. In one example, three sensors are equally spaced about the guard ring.

The guard ring can be coupled to a housing of the device. The coupling can include a flexible joint including a sliding joint or an elastic joint. The flexible joint allows relative movement between the guard ring and the housing. A sensor can be configured to measure a relative force at the interface between the guard ring and the housing.

In one example, the housing is affixed to the patient by a belt. The belt can have an adjustable length that can be adjusted to provide the biasing force. The biasing force can be measured in a direction substantially normal to a plane of the guard ring or the biasing force can be measured in terms of a tension force on a belt encircling a subject.

In one example, the biasing force on the guard ring is determined by a measurement of a tensile force on the belt in conjunction with an angle of departure of the belt relative to a contact surface of the guard ring.

According to one example, a force is applied on the crest of the stomach (the underside of the stomach, just below the navel) in order to flatten it out. When this area is relatively flat, the intra-uterine pressure can be measured by a force sensor of known area.

Figure 1:
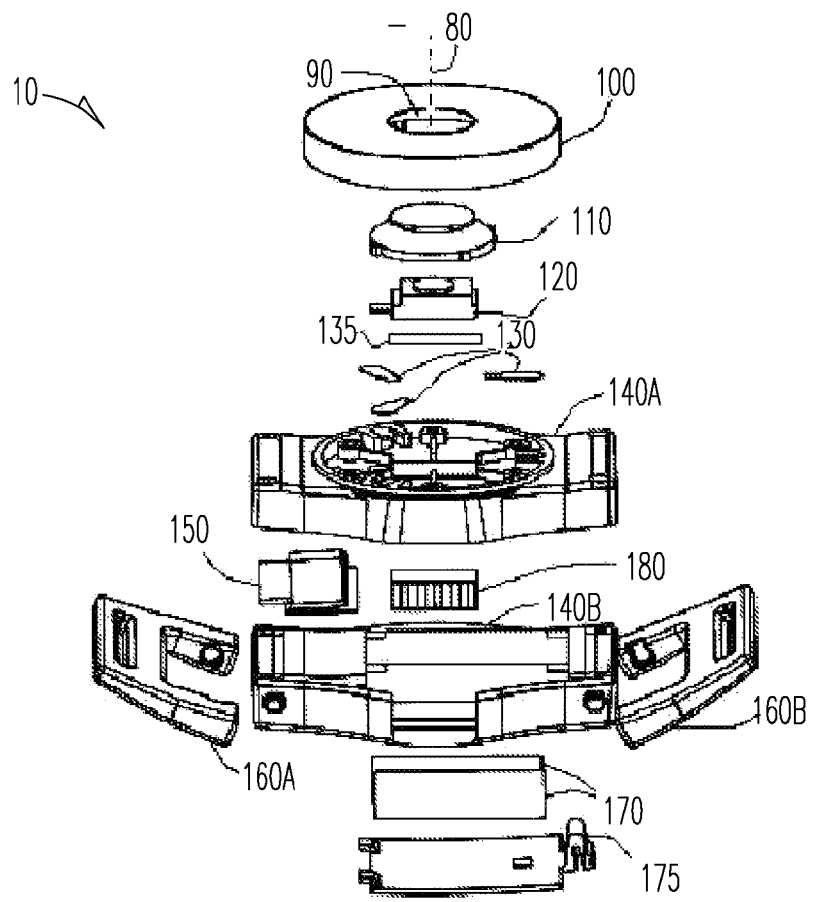
FIG. 1 illustrates an exploded view of one example of a device.

FIG. 1 illustrates an exploded view of example device 10. Device 10 includes guard ring 100, measurement sensor 120, and bias sensors 130.

Guard ring 100 is configured as a rigid circular member having aperture 90. Guard ring 100 and aperture 90 are shown aligned on axis 80. In use, the upper surface of guard ring 100 bears against the tissue (not shown) and is sometimes called a contact face. Axis 80, in use, is aligned normal to the tissue under measurement.

In the example shown, force transfer plate 110 is positioned in aperture 90 and is configured to transfer a pressure sensed at a membrane in the region of the aperture. Force transfer plate 110 carries a force to measurement sensor 120.

Guard ring 100 can be fabricated of a rigid material, such as plastic or metal. Force transfer plate 110 is fabricated of a rigid material configured to convey a force.

In the example shown, device 10 includes three bias sensors 130 however, other examples can include one or more sensors. Bias sensor 130 provides a measure of the force exerted on guard ring 100 in a direction parallel to axis 80. In the example shown, bias sensors 130 are distributed about the periphery of aperture 90. In one example, a measure of tension on a belt serves as a proxy for the normal force on guard ring 100.

Either one or both of measurement sensor 120 and bias sensor 130 can include an analog pressure sensor or a digital pressure sensor. A pressure sensor can include a force collector (such a diaphragm, piston, bourdon tube, or bellows) to measure strain (or deflection) due to applied force (pressure) over an area. A pressure sensor can include a piezoresistive strain gauge. A pressure sensor can include a capacitive sensor that uses a diaphragm and pressure cavity to create a variable capacitor to detect strain due to applied pressure. A pressure sensor can include an electromagnetic element that measures displacement of a diaphragm by means of changes in inductance (reluctance), Hall Effect, or by eddy current principle. A pressure sensor can include a piezoelectric element that uses a piezoelectric effect in certain materials such as quartz to measure the strain upon the sensing mechanism due to pressure. A pressure sensor can include an optical element that uses the physical change of an optical fiber to detect strain due to applied pressure. A pressure sensor can include a potentiometric element that uses the motion of a wiper along a resistive mechanism to detect the strain caused by applied pressure. A pressure sensor can include an active element or a passive element.

In the example shown, measurement sensor 120 is affixed to sensor platform 135. Sensor platform 135 is coupled to a housing, including top housing 140A and bottom housing 140B. Top housing 140A and bottom housing 140B carry electronic module 150. Electronic module 150 can be coupled to measurement sensor 120, bias sensor 130, and power supply 170. Electronic module 150 can include a printed circuit board, a flexible circuit board, a wireless telemetry system, a microprocessor, a digital circuit, an analog circuit, or other elements configured to implement an example of a method described herein. Power supply 170, including one or more batteries, is retained by battery cover 175.

In the example shown, top housing 140A provides a structural base for three bias sensors 130. Top housing 140A maintains the aforementioned components in alignment and facilitates application of the biasing force on the tissue. Bias sensors 130 provide a measure of the biasing force exerted by the guard ring on the tissue surrounding the region of the aperture.

Bottom housing 140B carries power supply 170, here shown as a pair of batteries, and battery cover 175. Electronic module 150, such as a circuit board, is positioned within a void between the top housing and a bottom housing.

Electronic module 150 is powered by the power supply 170. In one example, electronic module 150 includes circuitry for signal processing of the signal from measurement sensor 120, the signal (or signals) from biasing sensors 130, and provides telemetry with a remote device (not shown in the figure).

Belt clips 160A and 160B, shown in FIG. 1, are configured to engage a flat belt. In one example, the flat belt can be positioned to encircle the torso of a user. The belt clips allow the flat belt to be readily removable or adjustable without the need for tools.

FIG. 1 includes display 180 coupled to the housing. Display 180 is configured to display a visible indication corresponding to device 10. For example, display 180 can include a light emitting diode (LED) indicator configured to provide a measure of a biasing force exerted by guard member 100 as indicated by the bias sensors 130. Display 180 can include a color scale or color coded indication to provide visual information to a user. In one example, display 180 is configured to indicate a first color (such as red) to indicate that the biasing force is less than 1 kg, a second color (such as green) to indicate that the biasing force is between 1 and 2 kg, and a third color (such as red or yellow) to indicate that the biasing force is greater than 2 kg.

Other indications can also be provided. For example, display 180 can include a liquid crystal display (LCD) calibrated to indicate a numerical value or range of biasing force.

Display 180 can be configured to indicate a value or range corresponding to measurement sensor 120 associated with tissue at the site of aperture 90.

Electronic module 150 can include circuitry (digital or analog) to measure and store data concerning the biasing force. For example, the electronic module 150 can include a communication module to allow data telemetry with a remote device. The telemetered data can include a measure of the biasing force, a measure of the measured pressure, a measure of a temperature, a measure of oximetry or other indication based on one or more sensors coupled to the present subject matter.

Figure 2:
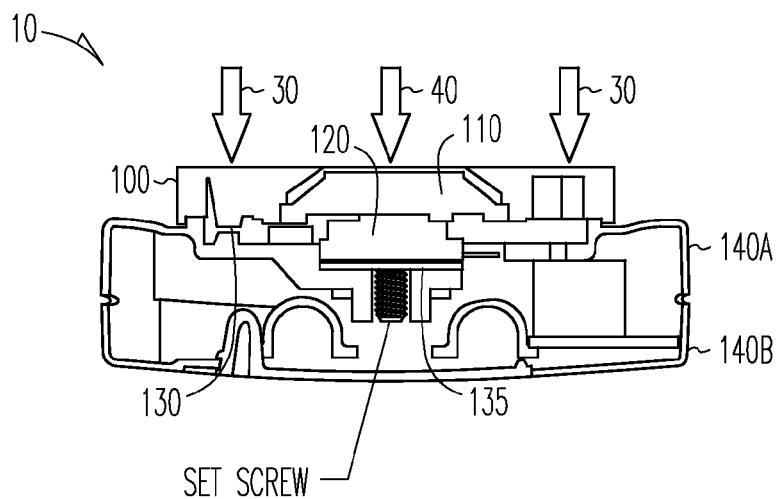
FIG. 2 illustrates a cross-sectional view of an example.

FIG. 2 illustrates a cross-sectional view of device 10 according to one example. In the figure, the guard ring force, at arrow 30, is aligned normal to the contact surface of guard ring 100. The intra-uterine force, at arrow 40, is shown applied to the region proximate aperture 90 of guard ring 100. Force transfer plate 110 conveys the intra-uterine force to measurement sensor 120. Measurement sensor 120 is positioned atop sensor platform 135. An adjustment screw threaded in the housing can provide calibration adjustment. Bias sensor 130 is positioned between guard ring 100 and a housing surface and provides a measure of the guard ring force or bias force.

Figure 3:
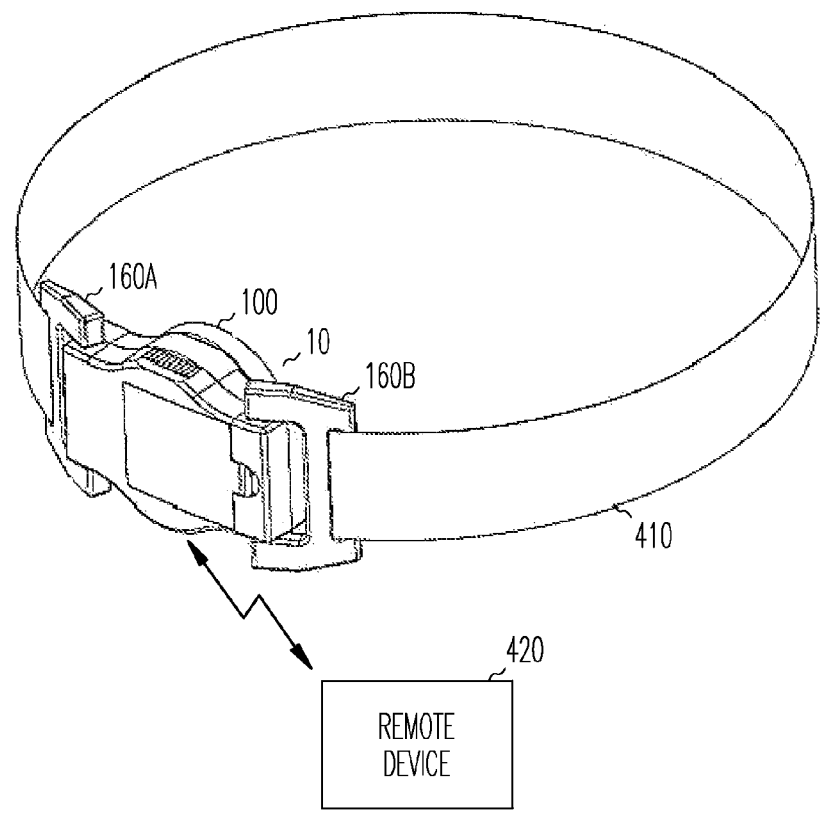
FIG. 3 includes an isometric view of a device with a belt according to one example.

FIG. 3 includes an isometric view of device 10 according to one example. The figure illustrates belt 410 having ends coupled to belt clips 160A and 160B. Belt clips 160A and 160B are affixed to opposing ends of the housing. The tension in belt 410 is user adjustable in order to control a biasing force exerted by the guard ring 100 of device 10. A portion of guard ring 100 is visible on an interior surface of device 10.

Device 10 is in wireless communication with remote device 420. Both device 10 and device 420 include wireless telemetry modules which, in various examples, includes Bluetooth or other RF communication circuitry.

Figure 4:
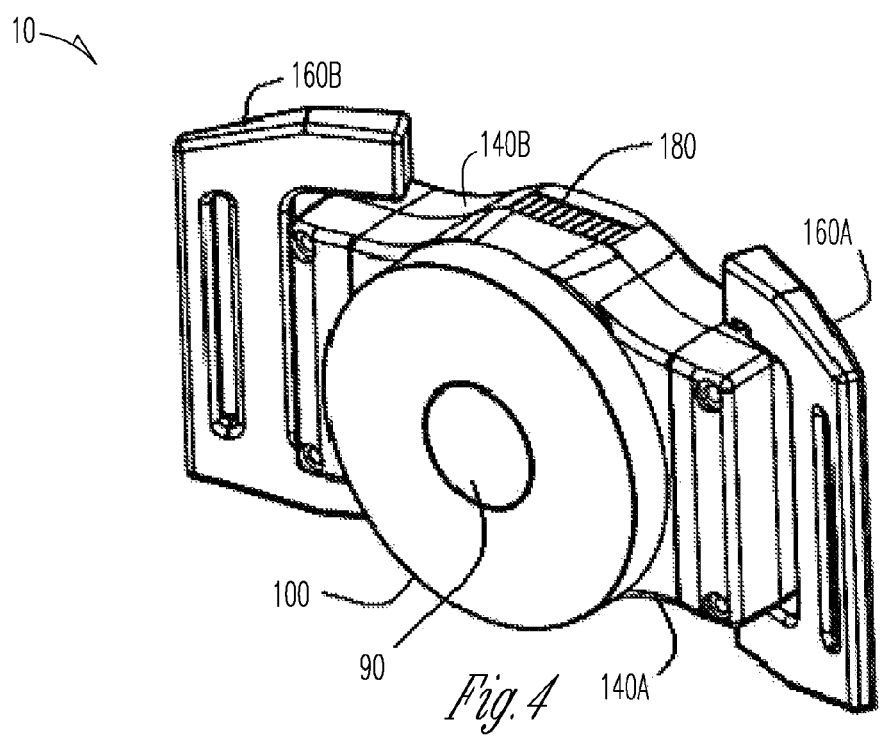
FIG. 4 illustrates an isometric view of an example device with the belt omitted for clarity.

FIG. 4 illustrates an isometric view of example device 10 with the belt omitted for clarity. The figure illustrates belt clips 160A and 160B and the guard ring 100 with a force transfer plate positioned at aperture 90. A display 180 is coupled to a portion of the housing. The display, in one example, includes an LED indicator.

Figure 5:
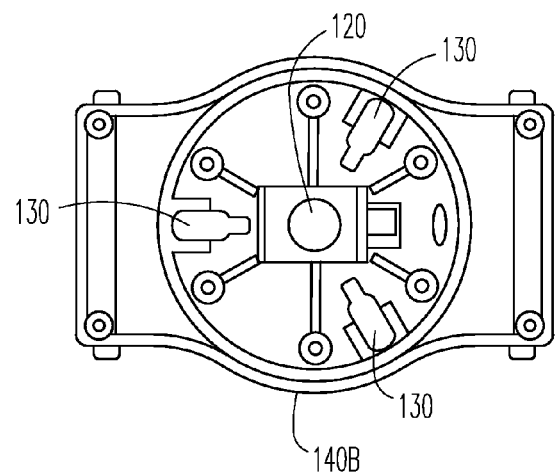
FIG. 5 illustrates a view of an example of a device in which the guard ring is omitted for clarity.

FIG. 5 illustrates a view of an example of device 10 in which guard ring 100 is omitted for clarity. In the figure, bias sensors 130 are illustrated located equidistant about the periphery of the guard ring. Measurement sensor 120 is located at the aperture of the guard ring.

Figure 6:
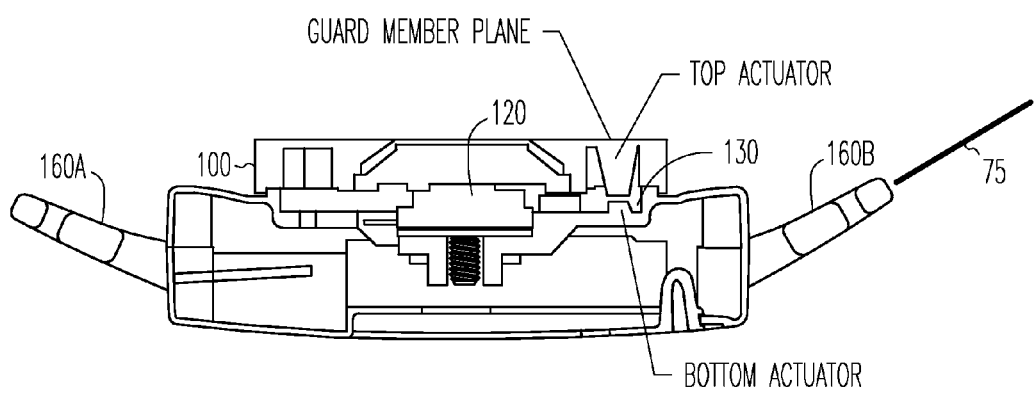
FIG. 6 illustrates a cross-sectional view of a device, according to one example.

FIG. 6 illustrates a cross-sectional view of a device, according to one example. In the example shown, belt clips 160A and 160B are positioned on opposing sides of the housing. Belt clips 160A and 160B are configured to sustain a tensile load and thereby urge guard ring 100 to exert a biasing force on the tissue. The biasing force can be measured by one or more bias sensors 130 configured to provide a signal as to the biasing force. In one example, a tensile sensor is responsive to a belt tension force and is used to provide a measure of the bias force. An angle measured relative to belt coupling line 75 and the contact face of the guard ring 100 (here denoted as guard member plane) provides data that can be used to determine the bias force. A suitably configured sensor can provide a measure of the angle between the contact face of the guard ring 100 and the belt coupling line 75.

Figure 7:
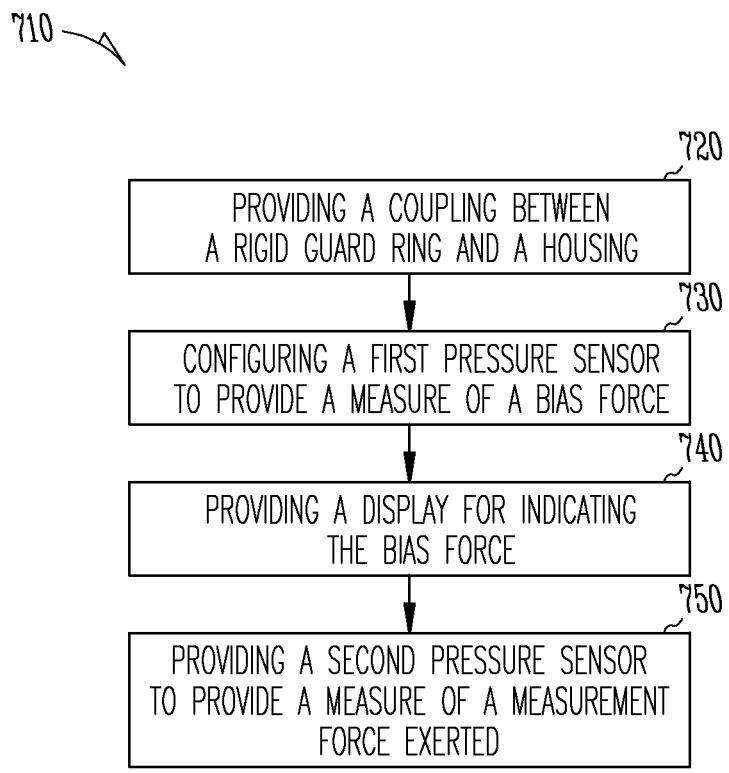
FIG. 7 includes a flow chart of a method according to one example.

FIG. 7 includes method 710 corresponding to one example of the present subject matter. Method 710, at 720, includes providing a coupling between a rigid guard ring and a housing. The coupling enables relative movement between the guard ring and the housing. At 730, the method includes configuring a first pressure sensor to provide a measure of a bias force exerted on the guard ring relative to the housing. At 740, the method includes providing a display for indicating the bias force. At 750, the method includes providing a second pressure sensor to provide a measure of a measurement force exerted by a membrane located proximate an aperture of the guard ring. Other configurations are also contemplated including providing an elastic coupling between the rigid guard ring and the housing. In one example, configuring the first pressure sensor includes configuring to provide a measure of a belt tension.

In one example, the guard ring includes three sensors configured to measure the applied force on the tissue from the guard ring. The guard ring force can be adjusted by tensioning a belt around the subject. In operation, one example is configured to provide a guard ring force in the range between 1-2 kg. At such a bias force, the intra-uterine force can be accurately measured by the measurement sensor through the force transfer plate.

The information can be wirelessly transmitted via Bluetooth (or other wireless communication protocol) to a remote device, such as a computer. The remote device can include a computer where both the guard ring and contractual forces are displayed. The guard ring force is also displayed on the device itself through an LED indicator.

A contraction of the uterine wall can be detected by the measurement sensor. The measurement sensor can indicate an absolute pressure measurement when a suitable bias force is applied using a guard ring. The bias force can be measured by multiple sensors distributed about the guard member and each of the multiple sensors can provide an independent sensor signal which, when resolved, indicates the bias force. The force detected by the individual bias sensors can be different or uniform.

The device is configured for easy placement and installation. One example is configured to allow a user to readily put on and remove the device without using tools.

The device is configured to execute software to display one or both of the guard ring force as well as the intra-uterine pressure.

A device includes a guard member, at least one bias sensor, a display, and a measurement sensor. The guard member includes an aperture on an axis. The at least one bias sensor is coupled to the guard member. The at least one bias sensor is configured to provide a bias signal corresponding to a bias force on the guard member. The bias force is aligned parallel with the axis. The display is coupled to the at least one bias sensor and is configured to provide a visible indication of the bias force. The measurement sensor is configured to provide an output signal corresponding to a measured force proximate the aperture.

In one example, the guard member includes a rigid ring. In one example, at least one bias sensor includes a force sensor. In one example, three sensors are positioned equidistant about the guard member. In one example, a belt or a strap is coupled to the guard member. The strap is configured to sustain a tensile load. The tensile load produces the bias force. The bias sensor includes a sensor coupled to the strap.

One example includes a method. The method includes exerting a peripheral force about a region of a compliant surface. The peripheral force is aligned normal to the surface. The method includes generating a visible indication of the peripheral force. The method includes generating a signal corresponding to a sensed force at the region.

In one example, the generating the visible indication includes illuminating a light emitting diode (LED). In one example, generating the signal corresponding to the sensed force includes exerting an opposing force on the region. In one example, generating the signal corresponding to the sensed force includes using a force sensor. One example includes adjusting the peripheral force to a predetermined value. Adjusting the peripheral force can include adjusting a strap.

Various Notes & Examples

The present subject matter includes a device that can accurately and noninvasively measure the contractions of a woman whose pregnancy. In particular, one example is configured for monitoring a pregnancy considered "at risk."

In various examples, a device is tailored for use in a home, a clinic or a medical care facility such as a hospital.

In one example, the device includes a switch coupled to the housing and allows a user to control the device operation. For example, a user operable switch can be operated to toggle the display between indicating the biasing force and indicating an aperture measurement force.

In one example, a user operable switch can be used to enter a threshold for an alarm. The alarm can be an audible or visible alert that can be rendered using a suitable sounder or display on the device itself or configured to signal an alert using a corresponding remote device.

Example 1 can include or use subject matter such as a device comprising a guard member, at least one bias sensor, a display, and a measurement sensor. The guard member has an aperture aligned on an axis. The at least one bias sensor is coupled to the guard member. The at least one bias sensor is configured to provide a bias signal corresponding to a bias force exerted on the guard member. The bias force is aligned parallel with the axis. The display is coupled to the at least one bias sensor and configured to provide a visible indication of the bias force. The measurement sensor is configured to provide an output signal corresponding to a measured force proximate the aperture.

Example 2 can include, or can optionally be combined with the subject matter of Example 1, to optionally include wherein the guard member includes a rigid ring.

Example 3 can include, or can optionally be combined with the subject matter of one or any combination of Examples 1 or Example 2, to optionally include wherein the at least one bias sensor includes a force sensor.

Example 4 can include, or can optionally be combined with the subject matter of one or any combination of Examples 1 through Example 3, to optionally include wherein the at least one bias sensor includes three sensors positioned equidistant about the guard member.

Example 5 can include, or can optionally be combined with the subject matter of one or any combination of Examples 1 through Example 4, to optionally include a belt coupled to the guard member. The belt is configured to sustain a tensile load. The tensile load corresponds to the bias force. The at least one bias sensor includes a sensor coupled to the belt.

Example 6 can include, or can optionally be combined with the subject matter of one or any combination of Examples 1 through Example 5, to optionally include wherein the belt includes an adjustor.

Example 7 can include, or can optionally be combined with the subject matter of one or any combination of Examples 1 through Example 6, to optionally include wherein the measurement sensor includes a force sensor.

Example 8 can include, or can optionally be combined with the subject matter of one or any combination of Examples 1 through Example 7, to optionally include a wireless communication module coupled to the measurement sensor.

Example 9 can include, or can optionally be combined with the subject matter of one or any combination of Examples 1 through Example 8, to optionally include a wireless communication module coupled to the at least one bias sensor.

Example 10 can include or use a system comprising a first device and a remote device. The first device has a guard ring, a display, a measurement sensor, and a first communication module. The guard ring has an aperture aligned with an axis. The guard ring is configured to provide a measure of a bias force aligned with the axis. The display is coupled to the guard ring and is configured to provide an indication of the bias force. The measurement sensor is configured to provide an output signal corresponding to a measured force proximate the aperture. The first communication module is coupled to the measurement sensor and configured to wirelessly communicate data corresponding to the output signal. The remote device is in wireless communication with the first communication module.

Example 11 can include, or can optionally be combined with the subject matter of Example 10 further including configuring the communication module to wirelessly communicate data corresponding to the bias force.

Example 12 can include or can optionally be combined with the subject matter of one or any combination of Example 10 or Example 11 to optionally include a belt coupled to the first device.

Example 13 can include or use subject matter such as a method comprising exerting a peripheral force about a region of a compliant surface. The force is aligned normal to the surface and relative to a housing. The method can include generating a visible indication of the peripheral force. The method can include generating an electric signal corresponding to a sensed force at the compliant surface.

Example 14 can include, or can optionally be combined with the subject matter of Example 13, to optionally include generating the visible indication includes illuminating a light emitting diode (LED).

Example 15 can include, or can optionally be combined with the subject matter of one or any combination of Example 13 or Example 14 to optionally include wherein generating the electric signal corresponding to the sensed force includes exerting an opposing force on the region.

Example 16 can include, or can optionally be combined with the subject matter of one or any combination of Example 13 through Example 15 to optionally include adjusting the peripheral force to a predetermined value.

Example 17 can include, or can optionally be combined with the subject matter of one or any combination of Example 13 through Example 16 to optionally include wherein adjusting the peripheral force includes adjusting a belt coupled to the housing.

Example 18 can include or use subject matter such as a method comprising providing a coupling between a rigid guard ring and a housing. The coupling enables movement between the guard ring and the housing. The method includes configuring a first pressure sensor to provide a measure of a bias force exerted on the guard ring relative to the housing. The method includes providing a display for indicating the bias force. The method includes providing a second pressure sensor to provide a measure of a measurement force exerted by a membrane located proximate an aperture of the guard ring.

Example 19 can include, or can optionally be combined with the subject matter of Example 18, to optionally include wherein providing the coupling includes providing an elastic coupling.

Example 20 can include, or can optionally be combined with the subject matter of Example 18 or Example 19, to optionally include wherein configuring the first pressure sensor includes configuring to provide a measure of a belt tension.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part.

The present subject matter can include a processor coupled to the circuit board. The processor can be configured to determine a bias force based on signals from the one or more bias sensors. In addition, the processor can be configured to determine a bias force based on a tensile load measurement exerted at the belt clips and based on the relative angle between the belt and the guard member. In one example, the processor can be configured to drive the display to indicate that the bias force is too low, too great, or within an acceptable range of force values. In one example, the processor can be configured to determine an absolute pressure based on a signal from the measurement sensor. In one example, the device is configured to wirelessly communicate with a remote device based on a predetermined protocol and in accordance with instructions executed on a processor.

Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device comprising:
    a guard member having an aperture aligned on an axis, the guard member movably coupled to a housing, the guard member including a rigid ring and having a contact face, the axis normal to the contact face, the contact face configured to engage a surface under measurement;
    at least one bias sensor coupled to the guard member, the at least one bias sensor configured to provide a bias signal corresponding to a bias force exerted on the guard member relative to the housing, the bias force aligned parallel with the axis;
    a display coupled to the at least one bias sensor and configured to provide a visible indication of the bias force;
    a force transfer plate positioned in the aperture, the force transfer plate configured for movement within the aperture in a direction parallel with the axis; and
    a measurement sensor coupled to the force transfer plate and configured to provide an output signal along a range corresponding to a measured force proximate the aperture.

2. The device of claim 1 wherein the at least one bias sensor includes a force sensor.

3. The device of claim 1 wherein the at least one bias sensor includes three sensors positioned equidistant about the guard member.

4. The device of claim 1 further including a belt coupled to the guard member, the belt configured to sustain a tensile load, the tensile load corresponding to the bias force, and wherein the at least one bias sensor includes a sensor coupled to the belt.

5. The device of claim 4 wherein the belt includes an adjustor.

6. The device of claim 1 wherein the measurement sensor includes a force sensor.

7. The device of claim 1 further including a wireless communication module coupled to the measurement sensor.

8. The device of claim 1 further including a wireless communication module coupled to the at least one bias sensor.

9. A system comprising:
    a first device having a guard ring, a display, a measurement sensor coupled to a force transfer plate, and a first communication module, the guard ring having an aperture aligned with an axis, the guard ring of a rigid material and having a contact face, the axis normal to the contact face, the contact face configured to engage a surface under measurement, the guard ring movably coupled to a housing and configured to provide a measure of a bias force relative to the housing and in a direction aligned with the axis, the display coupled to the guard ring and configured to provide an indication of the bias force, the measurement sensor configured to provide an output signal along a range corresponding to a measured force exerted on the force transfer plate, the force transfer plate disposed in the aperture and configured for movement within the aperture in a direction parallel with the axis, and the first communication module coupled to the measurement sensor and configured to wirelessly communicate data corresponding to the output signal; and
    a remote device in wireless communication with the first communication module.

10. The system of claim 9 further including configuring the communication module to wirelessly communicate data corresponding to the bias force.

11. The system of claim 9 further including a belt coupled to the first device.

12. A method comprising:
    exerting a peripheral force about a region of a compliant surface, the force exerted by a contact face of a rigid guard ring and the force aligned normal to the surface and relative to a housing, the force exerted at a periphery of an aperture of the guard ring;
    generating a visible indication of the peripheral force; and
    generating an electric signal corresponding to a sensed force at a force transfer plate disposed within the aperture, the force transfer plate configured for movement within the aperture in a direction normal to the surface and the sensed force along a range and corresponding to a pressure at the compliant surface.

13. The method of claim 12 wherein generating the visible indication includes illuminating a light emitting diode (LED).

14. The method of claim 12 wherein generating the electric signal corresponding to the sensed force includes exerting an opposing force on the region.

15. The method of claim 12 further including adjusting the peripheral force to a predetermined value.

16. The method of claim 15 wherein adjusting the peripheral force includes adjusting a belt coupled to the housing.

17. A method comprising:
    providing a coupling between a rigid guard ring and a housing, the coupling enabling movement between the guard ring and the housing;
    configuring a first pressure sensor to provide a measure of a bias force exerted on the guard ring relative to the housing;
    providing a display for indicating the bias force; and
    providing a second pressure sensor to provide a measure of a measurement force along a range and exerted on a force transfer plate, the force transfer plate configured for movement within an aperture of the guard ring by a membrane located proximate the aperture.

18. The method of claim 17 wherein providing the coupling includes providing an elastic coupling.

19. The method of claim 17 wherein configuring the first pressure sensor includes configuring to provide a measure of a belt tension.

* * * * *